(12) United States Patent
Raghavan et al.

(10) Patent No.: US 6,605,194 B2
(45) Date of Patent: Aug. 12, 2003

(54) SUBSTITUTED CALIX (4) PYRROLES AND PROCESS FOR THE SYNTHESIS OF CALIX (4) PYRROLES OVER MOLECULAR SIEVE CATALYSTS

(75) Inventors: Kondapuram Vijaya Raghavan, Andhra Pradesh (IN); Shivanand Janardan Kulkarni, Andhra Pradesh (IN); Motkuri Radha Kishan, Andhra Pradesh (IN); Nagabandi Srinivas, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/796,102

(22) Filed: Feb. 28, 2001

(65) Prior Publication Data

US 2002/0177705 A1 Nov. 28, 2002

(51) Int. Cl.$^7$ ............................................. C07D 487/22
(52) U.S. Cl. ................................... 204/157.72; 540/145
(58) Field of Search ...................... 540/145; 204/157.72

(56) References Cited

U.S. PATENT DOCUMENTS 6,262,257 B1 * 7/2001 Gale et al. .................. 540/145

FOREIGN PATENT DOCUMENTS

| WO | WO 9313150 | 7/1993 |
| WO | WO 9737995 | 10/1997 |

* cited by examiner

*Primary Examiner*—Mark L. Berch
*Assistant Examiner*—Kahsay Habte
(74) *Attorney, Agent, or Firm*—Dority & Manning, P.A.

(57) ABSTRACT

The present invention relates to novel calix pyrroles and a process for synthesis of calix (4) pyrroles by reacting pyrrole with cyclic or acyclic ketones in dichloro methane (DCM) solvent over molecular sieve catalysts which provides an eco-friendly, more economical and selective heterogeneous method.

29 Claims, 2 Drawing Sheets

1a : $R_1 = R_2 = CH_3$
2a : $R_1 = CH_3$, $R_2 = CH_2CH_3$
3a: $R_1 = R_2 = CH_2CH_3$

4a

5a: n=1
6a: n=3
7a: n=4

8a

1b : R₁ = R₂ = CH₃
2b : R₁ = CH₃, R₂ = CH₂CH₃
3b: R₁ = R₂ = CH₂CH₃

5b: n=1
6b: n=3
7b: n=4

8b

SUBSTITUTED CALIX (4) PYRROLES AND PROCESS FOR THE SYNTHESIS OF CALIX (4) PYRROLES OVER MOLECULAR SIEVE CATALYSTS

FIELD OF THE INVENTION

The present invention relates to novel calix (4) pyrroles and preparation of calix (4) pyrroles over zeolite molecular sieves. More particularly, this invention relates to a method for synthesis of calix (4) pyrroles directly from pyrroles and ketones in an eco-friendly zeolite catalyzed heterogeneous method with high yields.

This invention provides a non-corrosive eco-friendly process, where the catalyst is recyclable and reused many times, no work up procedure, no-wastage of the compounds (i.e. high atom selectivity), simple sample extraction and high selectivity of products.

BACKGROUND AND PRIOR ART REFERENCES

Calix pyrroles represent a subset of class of macrocycles that was previously termed as porphyrinogens. Porphyrinogens are non-conjugated macrocyclic species composed of four pyrrole rings linked to the position via $sp^3$ hybridized carbon atoms. Porphyrinogens that carry meso-hydrogen atoms are prone to oxidation to the corresponding phorphyrins and renamed the term porphyrinogen as calixpyrrole due to the analogues properties of calixarenes. Fully meso non-hydrogen substituted phorphyrongens are generally stable crystalline materials. The first such macrocycle, meso octamethyl calix (4) pyrrole was reported over a century ago by Bayer (Ber. Disctz. Chem. Ger. 1886, 19, 2184) using condensation between acetone and pyrrole catalyzed by HCl, however, the structure of the molecule was not elucidated. This method was refined by Dennstedt and Zimmerman (Ber. Disctz. Chem. Ger. 1887, 20, 850) by replacing the HCl with "chlorzink" and heating the reaction. Chelintzev and Toronov synthesized calix (4) pyrrole by the method of condensing acetone and pyrrole, methyl ethyl ketone and pyrrole, methyl hexyl ketone and pyrrole and a mixture of acetone and methyl ethyl ketone with pyrrole (J. Russ. Phys. Chem. Soc. 1916, 48, 1197; Chem Abstr. 1917, 11, 1418). Further, Chelintzev, Tronov and Kurmunov reported the production of calixpyrroles by condensing cyclohexanone with pyrrole and a mixture of acetone and cyclohexanone with pyrrole (J. Russ. Phys. Chem. Soc. 1916, 48, 1210). Rothenmund and Gage refined Dennstedt and Zimmermann's method by replacing the acid catalyst with methane sulphonic acid (J. Am. Chem. Soc. 1955, 55, 3740). In 1971, Brown, Iluichioson and Mackinon (Can. J. of Chem. 1971, 49, 4017) repeated the synthesis of mesotetracyclohexyl calixpyrrole and assigned a tetrameric macrocyclic structure. J. M. Lehn and coworkers have synthesized meso-octa-3-chloro propyl calix (4) pyrrole by an unpublished procedure and converted into meso-octa-3-cyano propyl calix pyrrole (B. Dietrich, P. Viout and J. M. Lehn in macrocyclic chemistry, VCH, Publishers, Weinhein 1993, pg82). The metal cation binding of deprotanated calix (4) pyrrole macrocyclics has been studied by Floriani and co-workers (Chem. Commun. 1996, 1257). Floriani has developed a method for expanding the pyrrole rings of metal bound deprotanated calix (4) pyrroles forming calix (1) pyridino (3) pyrroles and calix (2) pyridino (2) pyrroles (J. Am. Chem. Soc. 1995, 117, 2793). A further a prior art method reports using pyrrole, a $C_4$–$C_6$ saturated acyclic ketone and an acid containing vinyl groups are triple bonds to form a polymerized resin (WO 93/13150). In this case, the resulting products are undefined, since it appears to be unknown where the modifying group is attached to the product. By making use of calixarenes as templates P. A. Gale et al synthesized Calixarene-calix pyrrole dimers (calixarene capped-calixpyrrole) and expanded calixpyrroles (Tet Lett 37(44), 1996,7881) and also reported the synthesis of calixpyridino pyrroles and calix pyridines from calixpyrroles (Chem corn 1998, 1). Macrocycles have unexpected properties that make them particularly useful. Calixpyrroles bind anion and neutral molecular species in solution and in the solid state in such an effective and selective way the anions or neutral molecular species can be separated from other anions and neutral molecular species. Further the affinity a macrocycle has for a particular species can be 'tuned' by strategic choice of electron-donating or electron-withdrawing peripheral substituents for the synthesis of macrocycles.

According to W.O. Pat. No. 97/37995, various types of calixpyrroles was synthesized using different ketones including tetrahydrothiopyran-4-one, diphenylacetone, 10-nonadecanone, acetyl ferrocenes and chiral calixpyrroles by using chiral ketones. And also reported the synthesis of expanded calixpyrroles, where n>4, (i.e. Calix (5) pyrrole, Calix (6) pyrrole, calix (8) pyrroles), calix pyridino pyrroles, calix pyridines and their applications. Application of these properties for removal of biological ions or neutral molecule species for medical uses, removal of undesirable ions or neutral molecule species from environmental sources provides only a few of the practical and important uses.

These calix (4) pyrroles can be used in the dialysis of bodily fluids. Examples of dialyzable substrates include, but are not limited to phosphate containing molecules or halide waste (i.e. diabetes or drug overdoses and kidney dialysis).

Clean technology is fast replacing the various processes, which were once catalyzed by highly corrosive liquid acids, due to the growing concern for the environment. In these eco-friendly processes, solid acids which are highly selective and active with strong proton donating sites distributed uniformly within the pores, have been found to be an attracting replacement for the non-reusable, hazardous liquid acids. Porous materials created by nature or by synthetic have found great utility in all aspects of human activity. The pore structure of solids is usually formed in the stages of crystallization or subsequent treatment. Depending on their predominant pore size, the solid materials are classified as microporous, mesoporous and macroporous materials. The only class of porous materials possessing rigorously uniform pore sizes is that of Zeolites and related molecular sieves. Zeolites are uniform porous crystalline aluminosilicates and their lattice is composed by $TO_4$ tetrahedral (T=Al and Si) linked by sharing the apical oxygen atoms (Breck D. W., Zeolite molecular sieves: Structure, Chemistry and Use; Wiley and Sons; London 1974). As Zeolites act as sieves at the molecular level, these are considered as a subclass of molecular sieves. Zeolites have a number of interesting physical and chemical properties. The classes of phenomena that are of greatest practical importance are the availability to sorb organic and inorganic substances, to act as cation exchangers and to catalyze a wide variety of reactions. But due to the smaller pore size of these molecular sieves restricted their wide range applications, especially in case of larger molecules. But this has been overcome by the report of Mesoporous molecular sieves by Mobil researchers (C. T. Kresge, M. E. Leonowicz, W. J. Roth, J. C. Vartuli and J. S. Beck, Nature 359 (1992) 710) in 1992. These Mesoporous molecular sieve (MCM-41) has been opened a new era in the zeolite catalysis. Till then many reports have been published on the applications of this material for the catalytic activity towards oxidation, acylation and alkylation. And support material for enzymes, whole cell immobilization, and nano particles.

The previous processes have the disadvantage that (a) in all the cases mineral acids used as catalysts which are highly corrosive, (b) in all the cases inert atmosphere should be maintained, (c) in all the cases tedious work-up procedure is present, such as neutralization of acid etc, (c) separation and reusability of the catalyst is not possible, (d) in some cases more than a single step is carried out to get a particular calix pyrrole selectively, and (e) in some cases dry conditions should be maintained in order to obtain the corresponding compound.

Increasing the applications of these calix pyrroles demands an eco-friendly, environmentally clean, economical and free handling process. The present invention provides an eco-friendly process, which can overcome all the above drawbacks.

OBJECTS OF THE INVENTION

The main object of the present invention is to provide calix (4) pyrroles over zeolite molecular sieves, which is an eco-friendly heterogeneous catalytic method.

Another object of the present invention is to provide a process for the synthesis of novel calix (4) pyrroles such as tetraspirocycloheptyl calix (4) pyrrole, tetraspirocyclooctyl calix (4) pyrrole and tetraspiro (2-methylcyclohexyl) calix (4) pyrrole with sufficiently good yields.

Still another object of the present invention is to synthesize calix (4) pyrroles over molecular sieve catalysts under microwave irradiation, which is a solvent free reaction.

Yet another object is to provide a method wherein the kind and composition of calix (4) pyrrole can be varied within limits by a proper selection of catalyst.

Yet another object of this invention is to provide an efficient and economical method for synthesizing calix (4) pyrroles from pyrrole and ketones over solid acid catalysts.

SUMMARY OF THE INVENTION

The present invention relates to novel calix (4) pyrroles and a process for synthesis of calix (4) pyrroles as shown in FIGS. 1 to 8 of the accompanying drawings, from corresponding pyrrole and ketone over mesoporous molecular sieves. Macrocycles of the present invention can be selectively synthesized by taking the different pore sizes of the zeolites and by varying the reaction conditions.

DETAILED DESCRIPTION OF INVENTION

The present invention relates to novel calix (4) pyrroles and a process for synthesis of calix (4) pyrroles over mesoporous molecular sieves. The invention particularly relates to heterogeneous eco-friendly methodology for the synthesis of calix (4) pyrroles by using pyrrole and ketone in dichloromethane solvent. Specifically, the present invention relates to the synthesis calix (4) pyrroles from corresponding pyrrole and ketone over mesoporous (Mesoporous molecular sieve) MCM-41 molecular sieves with a high yield and selectivity. In an embodiment of the invention, the catalyst is selected from MCM-41, HZSM-5 (30), Hβ, HY and SAPO-5.

In another embodiment of the invention, the catalysts MCM-41, HZSM-5(30), Hβ, HY and SAPO-5 are conventional zeolite catalysts.

In another embodiment of the invention, the amount of catalyst used is ranging from 0.1 g to 1.0 g.

In still another embodiment of the invention, the solvent used for refluxing is selected from dichloromethane, methanol, and acetonitrile.

In yet another embodiment of the invention, the catalysts used are having the following surface area and pore size as given in the table below.

| Catalyst | Surface area (m²/g) | Pore size (Å) |
|---|---|---|
| MCM-41 | 980–1200 | 30–100 |
| HY | 525–625 | 6–8 |
| HZSM-5 (30) | 275–340 | 5–7.5 |
| SAPO-5 | 175–240 | 6.5–8.4 |
| Hβ | 600–680 | 5.5 × 6.6 to 7.5 × 8.5 |

In yet another embodiment of the invention, the pore size and surface area of the catalysts used in the reaction are given in the following table.

| Catalyst | Surface area (m²/g) | Pore size (Å) |
|---|---|---|
| HY | 593 | 7.3 |
| HZSM-5 (30) | 310 | 5.6 |
| SAPO-5 | 207 | 7.4 |
| Hβ | 640 | 6.5 × 7.6 |

In yet another embodiment of the invention, the molar ratio of pyrrole to ketone is selected in between 1:1 to 1:4.

In yet another embodiment of the invention, the cycloketone is selected from the group comprising cyclohexanone, cycloheptanone, cyclopentanone and cyclooctanone.

In yet another embodiment of the invention, the acyclic ketone is selected from the group comprising methyl ethyl ketone and 3-pentanone.

In yet another embodiment of the invention, acyclic products are obtained using the catalyst HY.

In yet another embodiment of the invention, major amounts of liner products are obtained using catalyst HZSM-5 (30).

In yet another embodiment of the invention, the yield of the calix (4) pyrrole is up to 70%.

In yet another embodiment of the invention, the selectivity of the calix (4) pyrrole is up to 90%.

In one more embodiment of preparing calix (4) pyrroles or tetraspiro calix (4) pyrroles, said method comprising mixing a pyrrole with a acyclic or cyclic ketones over a molecular sieve solid acid catalyst and subjecting the mixture to microwave radiation at a radiation level of about 2450 MHz (H1 power) for 3 to 10 minutes and optionally, refluxing using a solvent for extracting the compounds.

In another embodiment, the solvent used for refluxing is selected from dichloromethane, methanol, and acetonitrile.

In yet another embodiment of the present invention, in the equimolar reaction, the molar ratio of pyrrole to ketone is 1:1 and dichloromethane is used as a solvent for refluxing to obtain cyclic products.

In yet another embodiment, the catalyst used is mesoporus molecular sieve catalyst (MCM-41).

In yet another embodiment, the acyclic ketone used is acetone.

In yet another embodiment, the cyclic ketone used is cyclohexanone.

In yet another embodiment, the preparation of calix (4) pyrroles or tetraspiro calix (4) pyrroles is a solvent free process.

The catalyst can be synthesized from the well known defined methods. The starting materials used in the process are acyclic or cyclic ketones, which are readily available. Reacting the pyrrole with acyclic ketones which are selected from acetone ethyl ketone and 3-pentanone leads to form octamethyl calix (4) pyrrole, tetramethyl tetraethyl calix (4) pyrrole, and octaethyl calix (4) pyrroles correspondingly.

The catalyst MCM-41 (Mesoporous molecular sieve) prepared by an aqueous solution of aluminum isopropoxide (0.38 g) and to it an aqueous solution of sodium hydroxide (0.3 g) was added in 50 ml beaker and stirred in hot conditions, till a clear solution was formed. Then 9.4 ml of tetraethyl ammonium hydroxide (TEAOH) and Ludox colloidal silica (9.26 g) were added drop wise while stirring at room temperature. Then hexadecyl tri-methylammonium bromide (10.55 g) was added slowly to the above solution. The pH of the mixture was maintained at 11.0–11.5. Finally, the gel mixture was transferred into an autoclave and heated at 100° C. for 24 h. The solid product was recovered by filtration, washed with deionized water and dried in air. All the as-synthesized samples were calcined at 773K in air.

The catalyst weight can be varied in this reaction from 0.1 g to 1 g. The pyrrole to acetone molar ratio can be varied from 1:1 to 1:4.

In the reaction, an equimolar ratio of pyrrole and cyclohexanone was refluxed in dichloromethane (DCM) for 10 h in presence of MCM-41 catalyst. Along with the cyclized product, tetraspirocyclo hexyl calix (4) pyrrole 4a, the acyclic condensed products viz., dimer, trimer and tetramer (4b, 4c and 4d) were also formed.

In place of MCM-41 catalyst when HY was used, instead of cyclic product only the acyclic products were formed.

When HZSM-5 (30) was used as catalyst, along with the cyclized product calix (4) pyrrole, linear products also formed but the linear products are in major.

When Hβ was used as catalyst, along with the cyclized product calix (4) pyrrole, linear products are also formed.

The reaction time will be varied depending upon the nature of ketone and the catalyst.

In the one of equimolar reaction, pyrrole and acetone was mixed thoroughly and 0.5 gm of MCM-41 catalyst was added and then subjected to microwave irradiation for 3 min at a radiation level of about 2450 MHz and extract the compound by using dichloromethane as solvent, resulting low selectivity of cyclic product (1a). The reaction time is varied from 3 min to 10 min.

In another equimolar reaction, pyrrole and cyclohexanone was mixed thoroughly and added 0.5 gm of MCM-41 catalyst and then subjected to microwave irradiation for 3 min and extracted the compound by using dichloromethane as solvent, resulting low selectivity of cyclic product (4a). The reaction time is varied from 3 min to 10 min. The radiation level is maintained at about 2450 MHz.

Mixed calix pyrroles such as tetramethyl dicyclohexyl calix (4) pyrrole, hexamethyl cyclohexyl calix (4) pyrrole, dimethyl tri cyclohexyl calix (4) pyrrole has been obtained by reacting the acetone, cyclohexanone in required molar ratio over MCM-41 catalyst in dicholoromethane solvent by refluxing for 15 h.

Pore size and surface area of the catalysts plays a major role in this reaction.

All the catalysts were characterized by X-ray diffraction, Infrared spectroscopy, BET-surface area and $NH_3$-Temperature programmed desorption.

The inventors found that the dichloromethane (DCM) was better solvent than other solvents like methanol, acetonitrile. Acetone as solvent did not found the selectivity towards higher selectivity of octamethyl calix (4) pyrrole.

After the reaction was completed the catalyst was separated by filtration, then the solvent was vacuum evaporated and the residue was mounted on the silica column and the products were separated through n-hexane: ethylacetate (95:5) media and confirmed by $H^1$ NMR, $C^{13}$ NMR and Mass spectroscopy and for 1a, single crystal XRD also.

BRIEF DESCRIPTION OF THE ACCOMPANYING DRAWINGS

Figure 1:
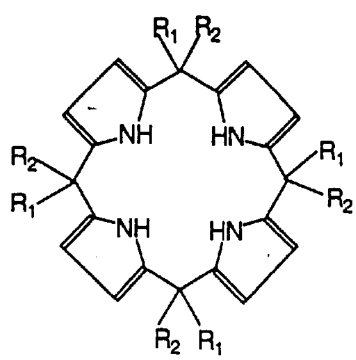
FIG. 1 shows structure of octa alkyl substituted calix (4) pyrrole, wherein $R_1$ and $R_2=CH_3$ for octamethyl calix (4) pyrrole (1a), $R_1=CH_3$ and $R_2=CH_2CH_3$ for Tetraethyl Tetra methyl calix (4) pyrrole (2a), and $R_1=R_2=CH_2CH_3$ for octaethyl calix (4) pyrrole (3a).
Figure 2:
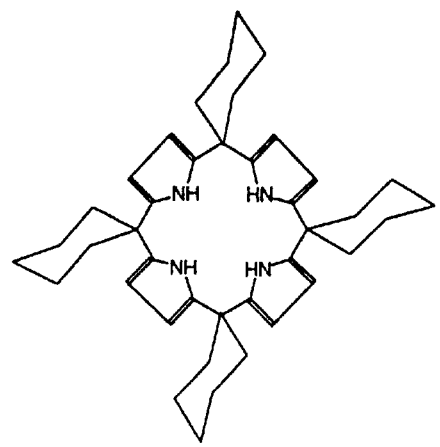
FIG. 2 shows structure of tetraspiro cyclohexyl calix (4) pyrrole (4a).
Figure 3:
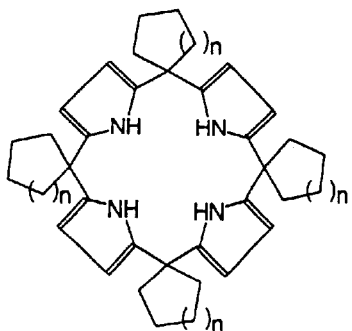
FIG. 3 shows structure of tetraspiro cycloalkyl substituted calix (4) pyrrole wherein, n=1 for tetraspiro cyclopentyl calix (4) pyrrole (5a), n=2 for tetraspiro cycloheptyl calix (4) pyrrole (6a), and n=4 for tetraspiro cyclooctyl calix (4) pyrrole (7a).
Figure 4:
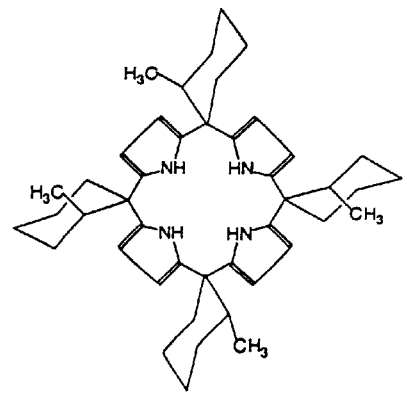
FIG. 4 shows structure of (2-methyl cyclohexyl) calix (4) pyrrole (8a).
Figure 5:
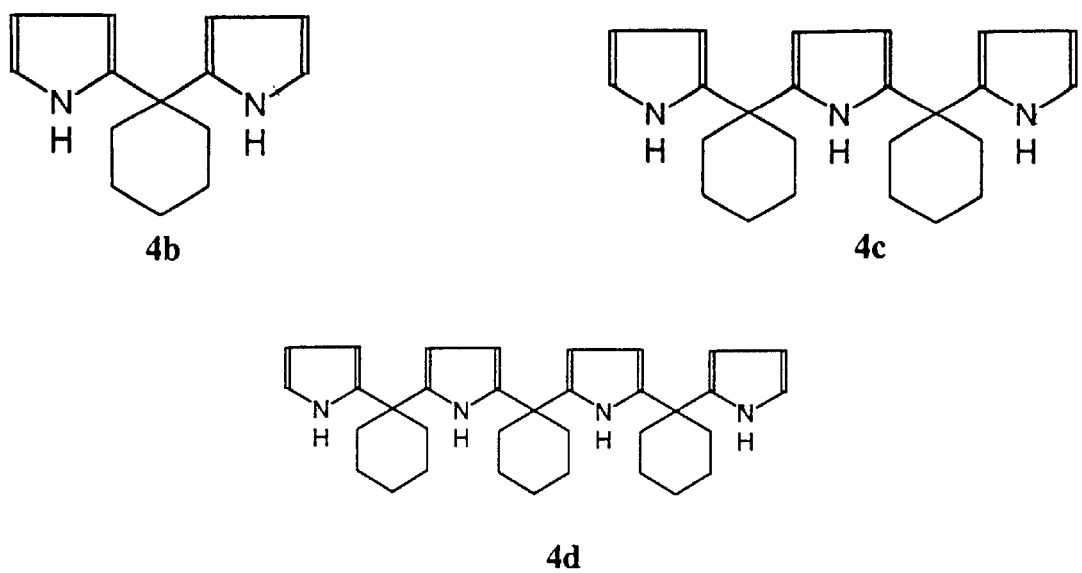
FIG. 5 shows structures of condensed products viz. dimer (4b), trimer (4c) and tetramer (4d).
Figure 6:
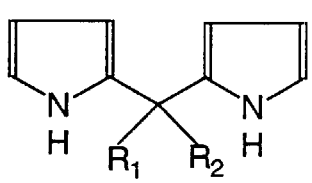

FIG. 6 shows structure of alkyl substituted linear (dimer) products, wherein $R_1$ and $R_2=CH_3$ for 1a, $R_1=CH_3$ and $R_2=CH_2CH_3$ for 2a, and $R_1=R_2=CH_2CH_3$ for 3a.

Figure 7:
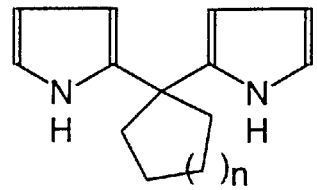

FIG. 7 shows structure of cyclic products, wherein n=1 for 5b; n=3 for 6b and n=4 for 7b.

Figure 8:
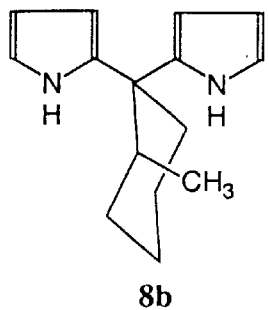

FIG. 8 shows structure of dimer product of 2-methylcyclohexyl (8b).

The process of this invention is described in further detail herein below by way of the following examples, which are only illustrative and are not intended to limit the scope of this invention.

EXAMPLES

Example 1

Synthesis of Octamethyl Calix (4) Pyrrole

In a 50 ml round bottom flask, 20 ml of dichloromethane (DCM) was introduced and 0.5 ml of pyrrole, 0.503 ml of acetone, and 0.5 g of MCM-41 catalyst were added to it. Then the reaction mixture was refluxed for 10 h. The cooled reaction mixture filtered, washed with DCM (5×10 ml). Then the solvent DCM was removed under reduced pressure and product was purified by column chromatography on silicagel (hexane eluent) affording the product as a white powder. The product was confirmed by NMR and Mass spectrometry. Yield of octamethyl calix (4) pyrrole was 67.5%; Selectivity was 73.0; Conversion of pyrrole was 92.4%. Selectivity was calculated as follows Selectivity=Yield/Conversion 1a: $^1$HNMR (200 MHz, $CDCl_3$): δ=1.49 (s, 24H, —$CH_3$), 5.85 (br, d, 8H; (pyrrole-βH), 6.89–6.99 (br, S, 4H, pyrrole-NH); HR-MS(EI): for calcd for $C_{28}H_{36}N_4$: calcd: 428.2939; found: 428.2938.

Example 2

In a 50 ml round bottom flask 20 ml of dichloromethane (DCM) was introduced and 0.5 ml of pyrrole, 0.503 ml of acetone, and 0.5 g of HZSM-5 (30) catalyst were added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The Results are as follows: Conversion of pyrrole is 81.4%.

| Product | Yield (wt %) | Selectivity (%) |
|---|---|---|
| Octamethyl calix(4)pyrrole (1a) | 40.0 | 49.2 |
| Trimer + tetramer | 29.8 | 36.6 |
| Dimer (1b) | 11.56 | 14.2 |

Example 3

In a 50 ml round bottom flask 20 ml of dichloromethane (DCM) was introduced and 0.5 ml of pyrrole, 0.503 ml of acetone, and 0.5 g of HY catalyst was added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 72.5%.

| Product | Yield (wt %) | Selectivity (%) |
|---|---|---|
| Octamethyl Calix(4)pyrrole | | |
| Trimer + tetramer | 14.0 | 19.3 |
| Dimer | 58.5 | 80.7 |

1b: $^1$HNMR (200 MHz, CDCl$_3$): δ=1.62 (s, 6H, —CH$_3$), 6.01–6.11 (m, 4H, pyrrole-βH), 6.48–6.56 (m, 2H, pyrrole-αH), 7.42–7.78 9br, s, 2H, NH), $^{13}$C NMR (50 MHz, CDCl$_3$): δ=29.30, 35.32, 103.74, 107.72, 117.03, 138.21; HR-MS (EI) for C$_{11}$H$_{14}$N$_2$: calcd: 174.1156; found: 174.1148

Example 4

Synthesis of tetramethyl tetraethyl calix (4) pyrrole

In a 50 ml round bottom flask 20 ml of dichloromethane (DCM) was introduced and 0.5 ml of pyrrole, 0.65 ml of Methyl ethyl ketone, and 0.5 g of Al-MCM-41 catalyst was added to it. Then the mixture was refluxed for 72 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 48.0%.

| Product | Yield (wt %) | Selectivity (%) |
|---|---|---|
| Tetraethyl tetramethyl calix(4)pyrrole (2a) | 34.8 | 72.5 |
| Trimer + tetramer | 4.5 | 9.4 |
| Dimer (2b) | 8.7 | 18.1 |

2a: $^1$HNMR (200 MHz, CDCl$_3$): δ=0.63–0.8 (t, J(H,H)=2 Hz, 12H), 1.34–1.48 (br, s, 12H, —CH$_3$), 1.86–1.96 (q, 8H, C$\underline{H_2}$CH$_3$), 5.85 (br, d, 8H), 6.89–7.09 (br, s, 4H, NH);$^{13}$C NMR (50 MHz, CDCl$_3$) 137.26, 103.75, 39.18, 33.21, 26.04, 8.65; HR-MS (EI) for C$_{32}$H$_{44}$N$_4$: calcd: 484.3565, found: 484.3561.

2b: $^1$HNMR (200 MHz, CDCl$_3$): δ=0.72–0.85 (t, J=8.37, 3H. —CH$_2$CH$_3$), 1.53 (s, 3H, —CH$_3$), 1.92–2.06 (q, J=4.65, 6.97 Hz, 2$\underline{H}$, —CH$_2$CH$_3$), 6.0–6.10 (m, 4H, pyrrole-βH), 6.50–6.58 (m, 2$\underline{H}$,pyrrole-αH), 7.6 (BR, S, 2H, pyrrole-NH). $^{13}$C NMR: 138.04, 116.29, 107.61, 104.66, 39.35, 33.63, 25.57, 8.91; HR-MS (EI) for C$_{12}$H$_{16}$N$_2$: calcd: 188.1313, found: 188.1317.

Example 5

Synthesis of octaethyl calix (4) pyrrole

In a 50 ml round bottom flask 20 ml of dichloromethane (DCM) was introduced and 0.5 ml of pyrrole, 0.73 ml of 3-Pentanone, and 0.5 g of Al-MCM-41 catalyst was added to it. Then the mixture was refluxed for 5 days. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 77.0%.

| Product | Yield (wt %) | Selectivity (%) |
|---|---|---|
| Octaethyl calix(4)pyrrole (3a) | 10.1 | 13.1 |
| Trimer + tetramer | 4.8 | 6.2 |
| Dimer (3b) | 62.1 | 80.7 |

3a: $^1$HNMR (200 MHz, CDCl$_3$): δ=5.85–5.93 (br, d, J (H,H)=2.27 Hz, 8H, pyrrole-βH), 6.96–7.05 (br, s, 4H, pyrrole-NH); HR-MS (EI) for C$_{36}$H$_{52}$N$_4$: calcd: 540.4191, found:540.4194.

3b: $^1$HNMR (200 MHz, CDCl$_3$): δ=0.68–0.76 (t, J=7.17, 6H, CH$_2$CH$_3$), 1.88–2.01 (q, J=5.12, 7.69 Hz, 4H, C$\underline{H_2}$—CH$_3$), 6.01–6.12 (br, s, 4H, pyrrole-βH), 6.5–6.59 (br, s, 2H), 7.45–7.65 (br, s, 2H, pyrrole-NH); HR-MS (EI) for C$_{13}$H$_{19}$N$_2$: calcd: 202.1469, found: 202.1475.

Example 6

Synthesis of tetraspiro cyclohexyl calix (4) pyrrole

In a 50 ml round bottom flask 20 ml of dichloromethane (DCM) was introduced and 0.5 ml of pyrrole, 0.75 ml of Cyclohexanone, and 0.5 g of calcined and dried Al-MCM-41 catalyst was added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 95.0%.

| Product | Yield (wt %) | Selectivity (%) |
|---|---|---|
| Tetraspirocyclohexyl calix(4)pyrrole (4a) | 70.3 | 74.0 |
| Trimer + tetramer | 12.4 | 13.0 |
| Dimer (4b) | 12.3 | 13.0 |

4a: $^1$H NMR (200 MHz, CDCl$_3$): δ=1.38–1.68(m,24H, cyclohexyl), 1.88–2.12(m,16H, cyclohexyl), 5.86 (br.d, 8H; pyrrole-βH), 6.95 (br.s, 4H, pyrrole NH), $^{13}$C NMR (50 MHz,CDCl$_3$): δ=22.75, 26.04, 37.17, 39.63, 103.44 (pyrrole-βH), 136.50(pyrrole-αH); HR-MS(EI) for C$_{40}$H$_{52}$N$_4$ (H$^+$): calcd: 588.4191; found: 588.4169.

Example 7

In a 50 ml round bottom flask 20 ml of dichloromethane (DCM) was introduced and 0.5 ml of pyrrole, 0.75 ml of Cyclohexanone, and 0.5 g of HZSM-5 (30) catalyst was added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: Conversion of pyrrole is 69.6%.

| Product | Yield (wt %) | Selectivity (%) |
|---|---|---|
| Tetraspirocyclohexyl Calix(4)pyrrole | 10.7 | 15.4 |
| Trimer + tetramer | 5.9 | 8.5 |
| Dimer | 53.0 | 76.1 |

Example 8

In a 50 ml round bottom flask 20 ml of dichloromethane (DCM) was introduced and 0.5 ml of pyrrole, 0.75 ml of Cyclohexanone, and 0.5 g of HY catalyst was added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 78.9%.

| Product | Yield (wt %) | Selectivity (%) |
|---|---|---|
| Tetraspirocyclohexylcalix (4) pyrrole | | |
| Trimer + tetramer | 16.2 | 20.5 |
| Dimer | 62.7 | 79.5 |

4b: $^1$H NMR (200 MHz, CDCl$_3$): δ=1.36–1.65(m,6H, cyclohexyl),1.95–2.12(m,4H,cyclohexyl,6.01–6.12(m,4H, pyrrole-βH), 6.45(br.d, 2H; pyrrole-αH), 7.32–7.68 (br.s, 2H, pyrrole NH); $^{13}$C NMR(50 MHz,CDCl$_3$): δ=22.17, 26.32, 37.65, 41.21, 104.64, 108.27,116.99, 139.21; HR-MS (EI) for C$_{14}$H$_{18}$N$_2$ (H$^+$): calcd: 214.1469; found: 214.1460.M+: 214(100%), 171,148

4d: HR-MS (EI) for C H N: calcd: 508.3546; found= 508.3565

Example 9

Synthesis of tetraspiro cyclopentyl calix (4) pyrrole

In a 50 ml round bottom flask 20 ml of dichloromethane (DCM) was introduced and 0.5 ml of pyrrole, 0.64 ml of Cyclopentanone, and 0.5 g of Al-MCM-41 catalyst was added to it. Then the mixture was refluxed for 20 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 74.3%.

| Product | Yield (wt %) | Selectivity (%) |
|---|---|---|
| Tetraspiro cyclopentyl calix(4)pyrrole (5a) | 62.7 | 84.4 |
| Trimer + tetramer | 7.3 | 9.8 |
| Dimer | 4.3 | 5.8 |

5a: $^1$HNMR (200 MHz, CDCl$_3$): δ=1.55–1.8 (m, 16H, cyclopentyl), 1.85–2.01 (m, 16H, cyclopentyl), 5.8 (br, d, J=0.38 Hz, 8H, pyrrole-βH),7.0 (br, s, 4H, pyrrole-NH); $^{13}$C NMR: (50 MHz, CDCl$_3$): 137.20 (pyrrole-αH), 103.04 (pyrrole-βH), 46.93, 39.02, 23.91; HR-MS (EI) for C$_{36}$H$_{44}$N$_4$: calcd: 532.3565, found: 532.6575.

Example 10

Synthesis of tetraspiro cycloheptyl calix (4) pyrrole

In a 50 ml round bottom flask 20 ml of dichloromethane (DCM) was introduced and 0.5 ml of pyrrole, 0.85 ml of Cycloheptanone, and 0.5 g of Al-MCM-41 catalyst was added to it. Then the mixture was refluxed for 3 days. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 69.8%.

| Product | Yield (wt %) | Selectivity (%) |
|---|---|---|
| Tetraspiro cycloheptyl calix(4)pyrrole (6a) | 26.7 | 38.3 |
| Trimer + tetramer | 15.7 | 22.5 |
| Dimer (6b) | 27.4 | 39.2 |

6a: $^1$HNMR (200 MHz, CDCl$_3$): δ=1.45–1.72 (m, 32H, cycloheptyl), 1.94–2.12 (m,16H, Cycloheptyl), 5.83 (br, d,8H, pyrrole-βH), 6.78–6.88 (br,s,4H,NH),; HR-MS (EI) for C$_{44}$H$_{60}$N$_4$: calcd: 644.4817, found: 644.4752.

6b: $^1$HNMR (200 MHz, CDCl$_3$): δ=2.12–2.26(m,8H, cycloheptyl), 2.42–2.58 (m,4H, cycloheptyl), 6.01–6.13 (m, 4H,pyrrole-βH), 6.52–6.61 (m,2H, pyrrole-αH),7.51–7.71 (br,s,2H, pyrrole-NH); HR-MS (EI) for C$_{15}$H$_{20}$N$_2$: calcd: 228.1626, found 228.1616.

Example 11

Synthesis of tetraspiro cyclo octyl calix (4) pyrrole

In a 50 ml round bottom flask 20 ml of dichloromethane (DCM) was introduced and 0.5 ml of pyrrole, 0.9 ml of Cyclooctanone, and 0.5 g of Al-MCM-41 catalyst was added to it. Then the mixture was refluxed for 5days. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 78.0%.

| Product | Yield (wt %) | Selectivity (%) |
| --- | --- | --- |
| Tetraspiro cyclooctyl calix(4)pyrrole (7a) | 8.3 | 10.6 |
| Trimer + tetramer | 23.7 | 30.4 |
| Dimer (7b) | 46.0 | 59.0 |

7a: $^1$HNMR (200 MHz, CDCl$_3$): δ=1.18–1.82 (m, 56H, cyclooctyl), 5.93 (br,d,8H, pyrrole-βH), 6.91–6.99 (br,s,4H, pyrrole-NH); HR-MS (EI) for C$_{48}$N$_{68}$N$_4$: calcd; 700.5443, found: 700.5456.

7b: $^1$HNMR (200 MHz, CDCl$_3$): δ=1.42–1.80(m,10H, cyclooctyl), 2.09–2.21(m,4H, cyclooctyl), 5.99–6.16 (m,4H, pyrrole-βH), 6.48–6.57 (m,2H,pyrrole-αH),7.42–7.69(br,s, 2H,pyrrole-NH),; HR-MS(EI) for C$_{16}$N$_{22}$N$_2$: calcd: 242.1782, found: 242.1777.

Example 12
Synthesis of tetraspiro (2-methylcyclohexyl) calix (4) pyrrole

In a 50 ml round bottom flask 20 ml of dichloromethane (DCM) was introduced and 0.5 ml of pyrrole, 0.875 ml of 2-Methyl cyclohexanone, and 0.5 g of Al-MCM-41 catalyst was added to it. Then the mixture was refluxed for 10 h. The cooled reaction mixture filtered, washed with DCM (5×10 ml). Then the solvent DCM was removed under reduced pressure and product was purified by column chromatography on silicagel (hexane eluent) the products were confirmed by NMR and estimation was done by high pressure thin layer chromatography (HPTLC). The results as follows: conversion of pyrrole is 60.2%.

| Product | Yield (wt %) | Selectivity (%) |
| --- | --- | --- |
| Tetraspiro (2-methylcyclohexyl) calix(4)pyrrole (8a) | 5.1 | 8.5 |
| Trimer + tetramer | 21.3 | 35.4 |
| Dimer (8b) | 33.8 | 56.1 |

8a: HR-MS (EI) for C$_{44}$H$_{60}$N$_4$: calcd: 644.4817, found 644.4847.

8b: $^1$HNMR (200 MHz, CDCl$_3$): δ=0.8(d,3H,J(H,H)=7.2 Hz,CH$_3$), 1.24–2.34(m,9H,cyclohexyl), 6.01–6.14 (m,4H, pyrrole-βH), 6.42–6.54 (m,2H,pyrrole-αH),7.48(br,s,2H, pyrrole-NH); HR-MS (EI) for C$_{15}$H$_{20}$N$_2$: calcd: 228.1626, found: 228.1634.

The Main Advantages of the Present Invention Are
1. The present invention is an improved process that comprises environmentally clean technology with low wastage, easy separable and reusability of the catalyst.
2. This method provides a selective heterogeneous catalyst with longer life.
3. The catalysts used in this process are easily separable by the simple filtration
4. It also provides a method wherein the kind and composition of calix (4) pyrrole can be varied within limits by a proper selection of catalyst.
5. Tetraspirocyclopentyl calix (4) pyrrole has been synthesized for the first time over the heterogeneous method as well as homogeneous method.
6. Tetraspirocycloheptyl calix (4) pyrrole has been synthesized for the first time over the heterogeneous method as well as homogeneous method.
7. Tetraspirocyclooctyl calix (4) pyrrole has been synthesized for the first time over the heterogeneous method as well as homogeneous method.
8. Tetraspiro (2-Methylcyclohexyl) calix (4) pyrrole has been synthesized for the first time over the heterogeneous method as well as homogeneous method.

The Salient Futures of the Process are
i) the present invention provides an improved process that comprises environmentally clean technology with low wastage, easy separable and reusability of the catalyst,
ii) the catalysts used in this process are easily separable by the simple filtration,
iii) this process provides an eco-friendly method with higher selectivity,
iv) a method provides a selective heterogeneous catalyst with longer life, and
v) a method wherein the kind and composition of calix (4)pyrrole can be varied within limits by a proper selection of catalyst and this invention provides an efficient and economical method for synthesizing calix (4)pyrroles from pyrrole and ketones over solid acid catalysts.

We claim:
1. A method of preparing a calix(4) pyrrole, said method comprising:
   (a) refluxing a pyrrole with an acyclic or cyclic ketone in the presence of a molecular sieve catalyst in an organic solvent at a temperature of about 100° C. for a period of between about 10 to about 72 hours;
   (b) cooling the reaction mixture of step (a) to room temperature;
   (c) filtering the solution of step (b) and washing the residue with an organic solvent to recover catalyst and to obtain a mother liquor;
   (d) evaporating to dryness the mother liquor of step (c) to obtain a solid;
   (e) washing the solid of step (d) with deionized water;
   (f) drying the washed solid of step (e) in air, followed by calcining at 373° K in air; and
   (g) purifying the calcined product of step (f) by column chromatography to obtain the calix (4) pyrrole.
2. A method as defined claimed in claim 1, wherein said catalyst is selected from the group consisting of MCM-41, HZSM-5 (30), Hβ, HY and SAPO-5.
3. A method as defined in claim 1, wherein said catalyst is employed in an amount from about 0.1 to about 1.0 gram.
4. A method as defined in claim 1, wherein said catalyst is selected from the group consisting of MCM-41 having a surface area of from about 980 to about 1200 square meters per gram and a pore size of from about 30 to about 100 Angstroms, HY having a surface area of from about 525 to about 625 square meters per gram and a pore size of from about 6 to about 8 Angstroms, HZSM-5(30) having a surface area of from about 275 to about 340 square meters per gram and a pore size of from about 5 to about 7.5 Angstroms, Hβ having a surface area of from about 600 to about 680 square meters per gram and a pore size of from about 5.5×6.6 to about 7.5×8.5 Angstroms, and SAPO-5 having a surface area of from about 175 to about 240 square meters per gram and a pore size of from about 6.5 to about 8.4 Angstroms.

5. A method as defined in claim 1, wherein said catalyst is selected from the group consisting of HY having a surface area of about 593 square meters per gram and a pore size of about 7.3 Angstroms, HZSM-5(30) having a surface area of about 310 square meters per gram and a pore size of about 5.6 Angstroms, Hβ having a surface area of about 640 square meters per gram and a pore size of about 6.5×7.6 Angstroms, and SAPO-5 having a surface area of about 207 square meters per gram and a pore size of about 7.4 Angstroms.

6. A method as defined in claim 1, wherein the organic solvent used for refluxing is selected from the group consisting of dichloromethane, methanol, and acetonitrile.

7. A method as defined in claim 1, wherein the molar ratio of the pyrrole to the ketone is between about 1:1 to about 1:4.

8. A method as defined in claim 1, wherein a cyclic ketone is refluxed with the pyrrole, said cyclic ketone being selected from the group consisting of cyclohexanone, 2-methyl cyclohexanone, cycloheptanone, cyclopentanone and cyclooctanone.

9. A method as defined in claim 1, wherein in an acyclic ketone is refluxed with the pyrrole, said acyclic ketone being selected from the group consisting of acetone, diethyl ketone, and methyl ethyl ketone.

10. A method as defined in claim 1, wherein the catalyst is HY.

11. A method as defined in claim 1, wherein the catalyst is HZSM-5(30) and the method forms a linear product.

12. A method as defined in claim 1, wherein the yield of the calix (4) pyrrole is at least about 70%.

13. A method as defined in claim 1, wherein the selectivity of the calix (4) pyrrole is at least about 90%.

14. A method as defined in claim 1, wherein the calix (4) pyrrole is selected from the group consisting of:
   i) octamethyl calix (4) pyrrole (formula 1a);
   ii) tetraethyl tetra methyl calix (4) pyrrole (formula 2a);
   iii) octaethyl calix (4) pyrrole (formula 3a);
   iv) tetraspiro cyclohexyl calix (4) pyrrole (formula 4a);
   v) tetraspiro cyclopentyl calix (4) pyrrole (formula 5a);
   vi) tetraspiro cycloheptyl calix (4) pyrrole (formula 6a);
   vii) tetraspiro cyclooctyl calix (4) pyrrole (formula 7a); and
   viii) (2-methyl cyclohexyl) calix (4) pyrrole (formula 8a):

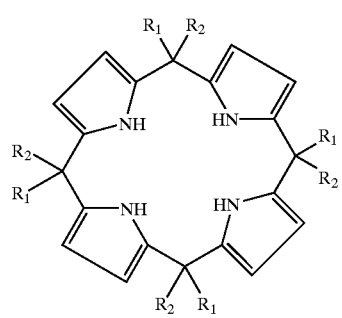

1a: $R_1 = R_2 = CH_3$
2a: $R_1 = CH_3, R_2 = CH_2CH_3$
3a: $R_1 = R_2 = CH_2CH_3$

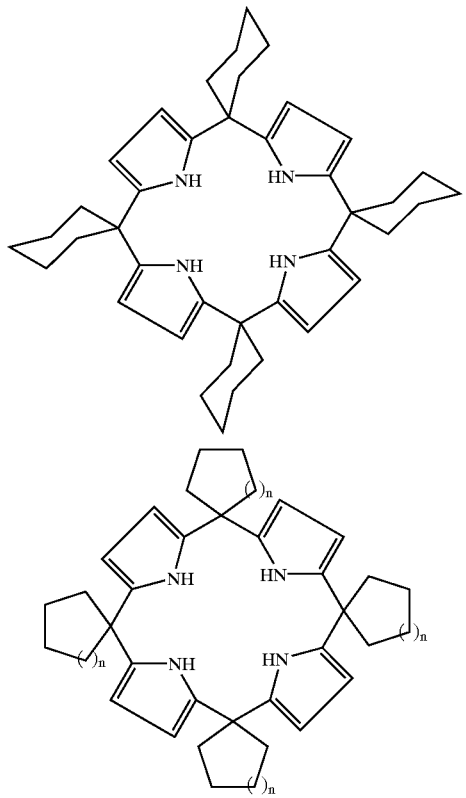

5a: n = 1
6a: n = 3
7a: n = 4

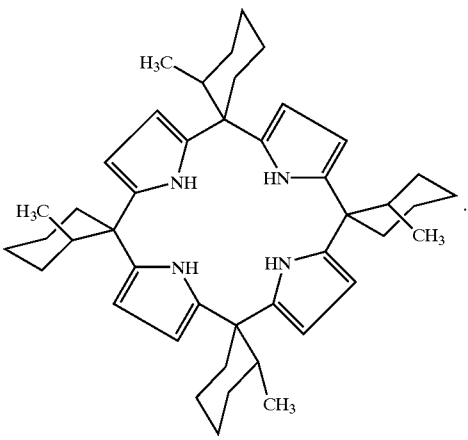

15. A method as defined in claim 1, wherein an acyclic product is formed by the method, said acyclic product being selected from the group consisting of:

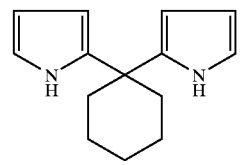

-continued

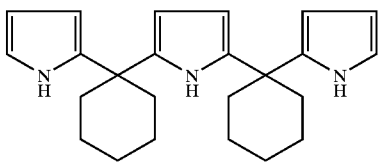
4c

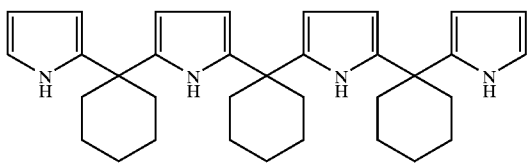
4d

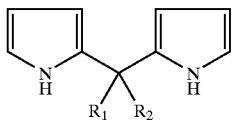

1b: $R_1 = R_2 = CH_3$
2b: $R_1 = CH_3, R_2 = CH_2CH_3$
3b: $R_1 = R_2 = CH_2CH_3$

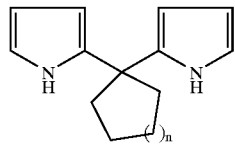

5b: n = 1
6b: n = 3
7b: n = 4

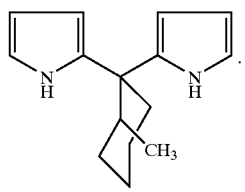
8b

16. A method for preparing a calix (4) pyrrole, said method comprising mixing a pyrrole with an acyclic or cyclic ketone over a molecular sieve solid acid catalyst, subjecting the mixture to microwave radiation for about 3 to about 10 minutes, and optionally, refluxing with a solvent to extract the calix (4) pyrrole.

17. A method as defined in claim 16, wherein the solvent is selected from the group consisting of dichloromethane, methanol, and acetonitrile.

18. A method as defined in claim 16, wherein the molar ratio of pyrrole to ketone is about 1:1.

19. A method as defined in claim 16, wherein the ketone is cyclohexanone, said pyrrole and said cyclohexanone being mixed in an equimolar ratio.

20. A method as defined in claim 16, wherein the catalyst is MCM-41.

21. A method as defined in claim 16, wherein the catalyst has a surface area of from about 980 to about 1200 meters squared per gram.

22. A method as defined in claim 16, wherein the catalyst has a pore size of from about 30 to about 100 Angstroms.

23. A method as defined in claim 16, wherein the microwave heating is carried out for a period of from about 2 minutes to about 15 minutes.

24. A method as defined in claim 16, wherein the microwave heating is carried out for a period of from about 3 minutes to about 10 minutes.

25. A method as defined in claim 16, wherein the microwave radiation level is about 2450 Megahertz.

26. A method as defined in claim 16, wherein an acyclic ketone is used that is selected from the group consisting of acetone, diethyl ketone, and methy ethyl ketone.

27. A method as defined in claim 16, wherein a cyclic ketone is used that is selected from the group consisting of cyclohexanone, 2-methyl cyclohexanone, cycloheptanone, cyclopentanone, and cyclooctane.

28. A method as defined in claim 16, wherein the calix (4) pyrrole is selected from the group consisting of:
  i) octamethyl calix (4) pyrrole (formula 1a);
  ii) tetraethyl tetra methyl calix (4) pyrrole (formula 2a);
  iii) octaethyl calix (4) pyrrole (formula 3a);
  iv) tetraspiro cyclohexyl calix (4) pyrrole (formula 4a);
  v) tetraspiro cyclopentyl calix (4) pyrrole (5a);
  vi) tetraspiro cycloheptyl calix (4) pyrrole (formula 6a);
  vii) tetraspiro cyclooctyl calix (4) pyrrole (formula 7a); and
  viii) (2-methyl cyclohexyl) calix (4) pyrrole (formula 8a):

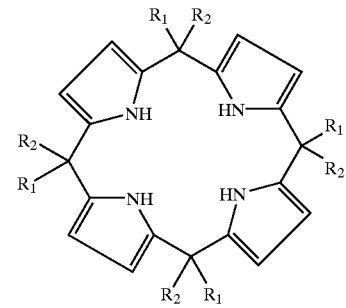

1a: $R_1 = R_2 = CH_3$
2a: $R_1 = CH_3, R_2 = CH_2CH_3$
3a: $R_1 = R_2 = CH_2CH_3$

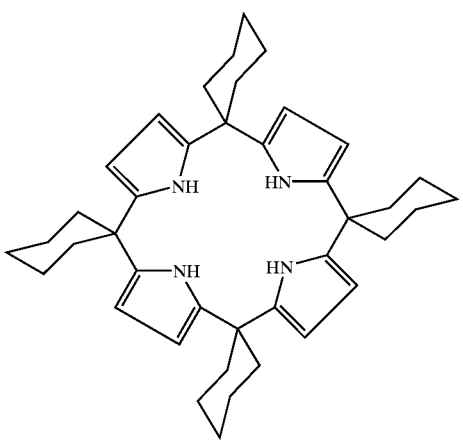
4a

-continued
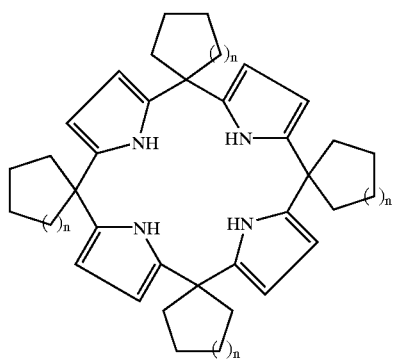
5a: n = 1
6a: n = 3
7a: n = 4
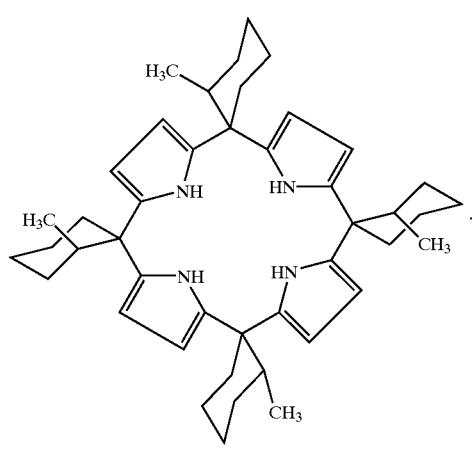
29. A method as defined in claim 16, wherein an acyclic product is formed by the method, said acyclic product being selected from the group consisting of:
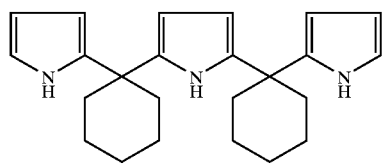
4b
-continued
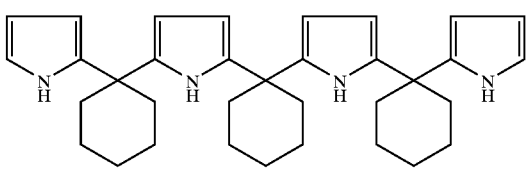
4c
4d
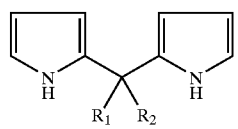
1b: $R_1 = R_2 = CH_3$
2b: $R_1 = CH_3$, $R_2 = CH_2CH_3$
3b: $R_1 = R_2 = CH_2CH_3$
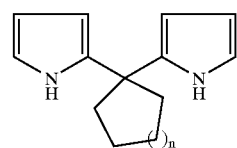
5b: n = 1
6b: n = 3
7b: n = 4
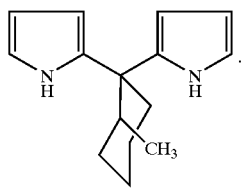
8b
* * * * *